(12) United States Patent
Wong et al.

(10) Patent No.: US 8,840,936 B2
(45) Date of Patent: Sep. 23, 2014

(54) HERBAL TEA WITHOUT EXCIPIENT USED AS MILK SUPPLEMENT AND METHOD OF PREPARING THE SAME

(75) Inventors: Suet Ying Wong, Hong Kong (CN); Kim Wu, Hong Kong (CN); Kuen Kuen Ella Lee, Hong Kong (CN)

(73) Assignee: Eu Yan Sang International Ltd, Singapore (SG)

( * ) Notice: Subject to any disclaimer, the term of this patent is extended or adjusted under 35 U.S.C. 154(b) by 0 days.

(21) Appl. No.: 13/576,123

(22) PCT Filed: Mar. 3, 2011

(86) PCT No.: PCT/CN2011/071479
§ 371 (c)(1),
(2), (4) Date: Jul. 30, 2012

(87) PCT Pub. No.: WO2012/088794
PCT Pub. Date: Jul. 5, 2012

(65) Prior Publication Data
US 2012/0301558 A1 Nov. 29, 2012

(30) Foreign Application Priority Data
Dec. 31, 2010 (CN) .......................... 2010 1 0624877

(51) Int. Cl.
*A61K 36/00* (2006.01)
*A61K 36/899* (2006.01)
*A23F 3/34* (2006.01)
*A61K 36/8998* (2006.01)
*A61K 36/8994* (2006.01)
*A61K 36/88* (2006.01)
*A23L 1/29* (2006.01)

(52) U.S. Cl.
CPC .............. *A61K 36/8994* (2013.01); *A23F 3/34* (2013.01); *A61K 36/8998* (2013.01); *A61K 36/899* (2013.01); *A61K 36/88* (2013.01); *A23L 1/296* (2013.01)
USPC ............ 424/725; 424/750; 424/776; 424/777

(58) Field of Classification Search
None
See application file for complete search history.

(56) References Cited

FOREIGN PATENT DOCUMENTS

WO    WO 2011/071479    3/2011

OTHER PUBLICATIONS

"Eu Yan Sang introduces Hong Kong's first-ever 'Sugar-Free' Infant's Digestive Support Formula Teabag," Eu Yan Sang Press Release, Dec. 16, 2011, 4 pages.

*Primary Examiner* — Chris R Tate
*Assistant Examiner* — Randall Winston
(74) *Attorney, Agent, or Firm* — Fish & Richardson P.C.

(57) ABSTRACT

The present invention relates to an herbal tea without excipient used as milk supplement. The herbal tea comprises the following medicinal materials: Raw *Semen Coicis*, *Herba Lophatheri*, *Setaria Italica*, Prepared *Semen Coicis*, *Fructus Hordei* Germinatus, *Fructus Setariae* Germinatus, *Medulla Junci* and *Triticum Aestivum*, wherein the *Triticum Aestivum* is used as a forming agent in the herbal tea. The method of preparing the herbal tea comprises the following steps: (a) weighing the medicinal materials according to the formula of herbal tea; (b) mixing the medicinal materials except for *Triticum Aestivum* together, decocting the resulting mixture with water 1-3 time(s), each time lasting for 0.5-2 hours, then combining the decoctions obtained from each time, filtering, and concentrating the resulting filtrate into a concentrated solution with relative density of 1.0-1.3 g/cm$^3$; (c) pulverizing the weighed *Triticum Aestivum* into particles of 15-40 mesh size, then dispersing the concentrated solution obtained from the step (b) to the pulverized particles of *Triticum Aestivum*; (d) fully drying the pulverized particles of *Triticum Aestivum* loaded with the concentrated solution obtained from the step (c), then packing the particles in a desired product form. The herbal tea of the present invention is specially suitable for babies who have trouble with intestine heat and stomach heat resulted from their long-term intake of milk product, since long-term intake of undesired components such as sucrose or other excipients which are not beneficial for their health is avoided.

10 Claims, No Drawings

HERBAL TEA WITHOUT EXCIPIENT USED AS MILK SUPPLEMENT AND METHOD OF PREPARING THE SAME

CROSS-REFERENCE TO RELATED APPLICATIONS

This application is a National Stage application under 35 U.S.C. §371 of International Application No. PCT/CN2011/071479, filed on Mar. 3, 2011, which claims the benefit of priority to Chinese Patent Application No. 201010624877.X, filed on Dec. 31, 2010. The disclosures of the prior applications are considered part of (and are incorporated by reference in) the disclosure of this application.

FIELD OF THE INVENTION

The present invention relates to an herbal tea and a method of preparing the same, and particularly relates to an herbal tea without excipient used as milk supplement and a method of preparing the same.

BACKGROUND OF THE INVENTION

Herbal tea used as milk supplement mainly aims at infantile intestine heat and stomach heat resulted from long-term intake of milk product. Accordingly, powdered milk is usually used in combination with the herbal tea used as milk supplement in order to relieve the intestine heat and stomach heat caused by intake of milk product.

Presently, two main types of herbal tea are available in the market. One type of herbal tea is in the form of traditional pack in which different raw materials of the formula of herbal tea are directly packed. This type of herbal tea requires users to decoct and concoct the different raw materials in person, which needs a long preparation time and results in different drug effects, even makes drug effects to vary greatly because of differences in the processes of decoction or concoction. Another type of herbal tea is in the form of ready-for-use granules, such products mostly contain excipients. Generally, excipients are inactive ingredients used as antiadherents, binders, disintegrants, and so on. For example, some excipients are used to give form or to help a drug to disintegrate into small particles for absorption. Typically, starch, lactose, sucrose and the like are used as excipients in drugs. However, starch is a kind of water-insoluble excipient which cannot be dissolved in water, it is therefore not suitable to be used as excipient in completely soluble granules. Moreover, it is not beneficial to baby's health to take in lactose, sucrose or other additives for a long time. For example, excessive intake of them will cause tooth decay, and long-term intake of them will cause obesity. In addition, blood sugar level of diabetic patients will rise due to long-term intake of sucrose. Also, some people may be allergic to some excipients—for example, many people are lactose-intolerant.

Therefore, in order to overcome the above-mentioned deficiencies existing in the prior art, there is a need to develop a ready-for-use herbal tea without excipient used as milk supplement.

SUMMARY OF THE INVENTION

One objective of the present invention is to provide a ready-for-use herbal tea without excipient used as milk supplement.

In order to realize the above objective, the present invention provides a technical solution as follows: an herbal tea without excipient used as milk supplement comprises the following medicinal materials: Raw *Semen Coicis*, *Herba Lophatheri*, *Setaria Italica*, Prepared *Semen Coicis*, *Fructus Hordei* Germinatus, *Fructus Setariae* Germinatus, *Medulla Junci* and *Triticum Aestivum*, wherein the *Triticum Aestivum* is used as a forming agent in the herbal tea.

In the herbal tea without excipient used as milk supplement according to the present invention, the weight percentages of the above medicinal materials are preferably as follows: 20-35% of Raw *Semen Coicis*, 5-15% of *Herba Lophatheri*, 5-15% of *Setaria Italica*, 5-15% of Prepared *Semen Coicis*, 4-12% of *Fructus Hordei* Germinatus, 4-12% of *Fructus Setariae* Germinatus, 0.2-2% of *Medulla Junci*, and 15-25% of *Triticum Aestivum*, based on the total weight of the medicinal materials.

According to a further preferred embodiment of the present invention, the weight percentages of the medicinal materials are as follows: 22-32% of Raw *Semen Coicis*, 8-15% of *Herba Lophatheri*, 8-15% of *Setaria Italica*, 6-12% of Prepared *Semen Coicis*, 5-10% of *Fructus Hordei* Germinatus, 5-10% of *Fructus Setariae* Germinatus, 0.2-1% of *Medulla Junci*, and 18-22% of *Triticum Aestivum*, based on the total weight of the medicinal materials.

According to a furthermore preferred embodiment of the present invention, the weight percentages of the medicinal materials are as follows: 29.10% of Raw *Semen Coicis*, 12.60% of *Herba Lophatheri*, 12.60% of *Setaria Italica*, 10.10% of Prepared *Semen Coicis*, 7.60% of *Fructus Hordei* Germinatus, 7.60% of *Fructus Setariae* Germinatus, 0.40% of *Medulla Junci*, and 20.00% of *Triticum Aestivum*, based on the total weight of the medicinal materials.

In addition, it should be noted that the above basic formula can be adjusted by adding other medicinal materials to meet various demands of customers. For example, the addition of *Pseudostellariae Radix* can strengthen the effect of invigorating spleen and replenishing qi, and the effect of moistening lung and promoting production of body fluids; the addition of *Radix Ophiopogonis* can strengthen the effect of nourishing yin and promoting production of fluid, and the effect of moistening lung and promoting production of body fluids; the addition of *Semen Lablab Album* can strengthen the effect of invigorating spleen for eliminating dampness, and the effect of regulating stomach and relieving summer heat. Similarly, a skilled person in the art can add other different medicinal materials into the basic formula of herbal tea as required. Furthermore, it will be appreciated by those skilled in the art that such modification based on the basic formula of herbal tea should fall into the scope of the present invention as defined by the appended claims.

In addition, the present invention further provides a method of preparing the herbal tea without excipient used as milk supplement of the invention, which comprises the following steps:

(a) weighing the medicinal materials according to the formula of herbal tea;

(b) mixing the medicinal materials except for *Triticum Aestivum* together, decocting the resulting mixture with water 1-3 time(s), each time lasting for 0.5-2 hours, then combining the decoctions obtained from each time, filtering, and concentrating the resulting filtrate into a concentrated solution with relative density of 1.0-1.3 g/cm$^3$;

(c) pulverizing the weighed *Triticum Aestivum* into particles of 15-40 mesh size, then dispersing the concentrated solution obtained from the step (b) to the pulverized particles of *Triticum Aestivum*;

(d) fully drying the pulverized particles of *Triticum Aestivum* loaded with the concentrated solution obtained from the step (c), then packing the particles in a desired product form.

In the method of preparing the herbal tea without excipient used as milk supplement according to the present invention, the step (b) preferably comprises the following steps: mixing the other medicinal materials except for *Triticum Aestivum* together, decocting the resulting mixture with water 2 times, each time lasting for 1 hour, then combining the decoctions obtained from each time, filtering, and concentrating the filtrate into a concentrated solution with relative density of 1.1-1.2 g/cm³ which is determined at 45-50° C.

In the method of preparing the herbal tea without excipient used as milk supplement according to the present invention, the step (c) preferably comprises the following steps: pulverizing the weighed *Triticum Aestivum* into particles of 25-35 mesh size, then spraying the concentrated solution obtained from step (b) to the pulverized particles of *Triticum Aestivum* by utilizing flow layer drying equipment; further preferably, the weighed *Triticum Aestivum* is pulverized into particles of about 30 mesh size in the step (c).

In the method of preparing the herbal tea without excipient used as milk supplement according to the present invention, the step (d) preferably comprises the step of packing the particles in tea bags.

In addition, it should be noted that, when the herbal tea comprises other medicinal materials besides those of the basic formula, effective ingredients can be extracted from the other medicinal materials by using conventional methods in the field of Chinese medicinal preparations according to the characteristics of the medicinal materials; alternatively, the other medicinal materials can be mixed with those of the basic formula, and the resulting mixture is decocted with proper amount of water, then the herbal tea can be prepared according to the method of the present invention mentioned above.

Compared with the prior herbal tea, the herbal tea used as milk supplement according to the present invention has the following advantageous effects:

The technical solution of the present invention is a breakthrough of conventional formula and preparation method of herbal tea used as milk supplement in the prior art. *Triticum Aestivum* is used as the forming agent, and at the same time it is used as one of the raw materials of the herbal tea which has an effect of removing deficient heat. The main reason for replacing conventional excipients with *Triticum Aestivum* is that *Triticum Aestivum* can absorb an extracted solution more easily than other raw materials. Because the effective ingredients extracted from other raw materials are dispersed into the pulverized particles of *Triticum Aestivum* and the resulting particles loaded with the effective ingredients are packed in tea bags, the concentrated solution can be released immediately and all active ingredients can fully diffuse into water when the herbal tea is taken mixed with boiled water. Compared to the direct use of raw medicinal materials, the effective ingredients of herbal tea of the present invention can be released more easily. Additionally, since the pulverized particles of *Triticum Aestivum* are packed in tea bags, solid residue cannot be released in water. Furthermore, due to the use of very mature preparing technology and equipments in the field of Chinese medicinal preparations, the method of the present invention has proved easy to perform with high production efficiency.

Because the present invention provides the above formula and preparation method, users can avoid long-term intake of excipients or other undesired components. Particularly, the herbal tea of the present invention is specially suitable for babies who have trouble with intestine heat and stomach heat resulted from their long-term intake of milk product, since long-term intake of undesired components such as sucrose or other excipients which are not beneficial for their health is avoided. Moreover, the herbal tea of the present invention is also suitable for diabetic patients.

Since the concentrated solution containing active ingredients is absorbed into the pulverized particles of *Triticum Aestivum*, the concentrated solution can be released immediately and the active ingredients fully diffuse in water once it contacts with water. Therefore, the herbal tea of the present invention can even be taken after being mixed with warm boiled water. Moreover, the herbal tea of the present invention is economic and highly efficient.

DETAILED DESCRIPTION OF PREFERRED EMBODIMENTS

The herbal tea without excipient used as milk supplement and the method of preparing the same according to the present invention will be described in detail by the following embodiments. It should be understood, however, that the invention is not limited to the following embodiments, and the invention may be varied in other manner so as not depart from the spirit and scope of the invention.

EXAMPLES

Example 1

The medicinal materials of herbal tea of the present invention are weighed according to the following weight percentages: 29.10% of Raw *Semen Coicis*, 12.60% of *Herba Lophatheri*, 12.60% of *Setaria Italica*, 10.10% of Prepared *Semen Coicis*, 7.60% of *Fructus Hordei* Germinatus, 7.60% of *Fructus Setariae* Germinatus, 0.40% of *Medulla Junci*, 20.00% of *Triticum Aestivum*. The total weight of the above eight medicinal materials is 100 g. Seven medicinal materials, namely Raw *Semen Coicis*, *Herba Lophatheri*, *Setaria Italica*, Prepared *Semen Coicis*, *Fructus Hordei* Germinatus, *fructus setariae* germinates and *Medulla Junci*, are mixed together. The resulting mixture is decocted with water 2 times, and each decocting time lasts for 1 hour, then the decoctions obtained from each time are combined and filtered. Thereafter, the resulting filtrate is concentrated into a concentrated solution with relative density of about 1.1 g/cm³ (45-50° C.) and the weight of the concentrated solution is 40 g. The weighed *Triticum Aestivum* is pulverized into particles of about 30 mesh size, and the concentrated solution is sprayed into the pulverized particles of *Triticum Aestivum* by utilizing flow layer drying equipment. The pulverized particles of *Triticum Aestivum* loaded with the concentrated solution are fully dried into 20 g of final product, which is packed in tea bags of 2 grams/bag and 10 bags/box.

Example 2

The medicinal materials of herbal tea used as milk supplement of the present invention are weighed according to the following weight percentages: 25.00% of Raw *Semen Coicis*, 10.60% of *Herba Lophatheri*, 10.60% of *Setaria Italica*, 8.10% of Prepared *Semen Coicis*, 7.60% of *Fructus Hordei* Germinatus, 7.60% of *Fructus Setariae* Germinatus, 0.40% of *Medulla Junci*, 20.00% of *Triticum Aestivum*, 10.10% of *Pseudostellariae Radix*. The total weight of the above nine medicinal materials is 100 g. The above eight medicinal materials except for *Triticum Aestivum* are mixed together. The resulting mixture is decocted with water 2 times, and each decocting time lasts for 1 hour, then the decoctions obtained from each time are combined and filtered. Thereafter, the resulting filtrate is concentrated into a concentrated solution with relative density of about 1.1 g/cm³ (45-50° C.) and the weight of the concentrated solution is 40 g. The weighed *Triticum Aestivum* is pulverized into particles of about 30 mesh size, and the concentrated solution is sprayed into the pulverized particles of *Triticum Aestivum* by utilizing flow layer drying equipment. The pulverized particles of *Triticum Aestivum* loaded with the concentrated solution are fully dried into 20 g of final product, which is packed in tea bags of 2 grams/bag and 10 bags/box.

In this example, *Pseudostellariae Radix* is added into the basic formula of herbal tea used as milk supplement of the present invention. Therefore, the herbal tea prepared in this example not only has the essential functions described above, but also can strengthen the effect of invigorating spleen and replenishing qi, and the effect of promoting production of fluid and moistening lung.

Example 3

The medicinal materials of herbal tea used as milk supplement of the present invention are weighed according to the following weight percentages: 25.00% of Raw *Semen Coicis*, 10.60% of *Herba Lophatheri*, 10.60% of *Setaria Italica*, 8.10% of Prepared *Semen Coicis*, 7.60% of *Fructus Hordei* Germinatus, 7.60% of *Fructus Setariae* Germinatus, 0.40% of *Medulla Junci*, 20.00% of *Triticum Aestivum*, 10.10% of *Radix Ophiopogonis*. The total weight of the above nine medicinal materials is 100 g. The above eight medicinal materials except for *Triticum Aestivum* are mixed together. The resulting mixture is decocted with water 2 times, and each decocting time lasts for 1.5 hours, then the decoctions obtained from each time are combined and filtered. Thereafter, the resulting filtrate is concentrated into a concentrated solution with relative density of about 1.2 g/cm³ (45-50° C.) and the weight of the concentrated solution is 40 g. The weighed *Triticum Aestivum* is pulverized into particles of about 30 mesh size, and the concentrated solution is sprayed into the pulverized particles of *Triticum Aestivum* by utilizing flow layer drying equipment. The pulverized particles of *Triticum Aestivum* loaded with the concentrated solution are fully dried into 20 g of final product, which is packed in tea bags of 2 grams/bag and 10 bags/box.

In this example, *Radix Ophiopogonis* is added into the basic formula of herbal tea of the present invention. Therefore, the herbal tea prepared in this example not only has the essential functions described in the invention, but also can strengthen the effect of nourishing yin for promoting production of fluid, and the effect of moistening lung and promoting production of fluid.

Example 4

The medicinal materials of herbal tea used as milk supplement of the present invention are weighed according to the following weight percentages: 25.00% of Raw *Semen Coicis*, 10.60% of *Herba Lophatheri*, 10.60% of *Setaria Italica*, 8.10% of Prepared *Semen Coicis*, 7.60% of *Fructus Hordei* Germinatus, 7.60% of *Fructus Setariae* Germinatus, 0.40% of *Medulla Junci*, 20.00% of *Triticum Aestivum*, 10.10% of *Semen Lablab Album*. The total weight of the above nine medicinal materials is 100 g. The above eight medicinal materials except for *Triticum Aestivum* are mixed together. The resulting mixture is decocted with water 3 times, and each decocting time lasts for 0.8 hour, then the decoctions obtained from each time are combined and filtered. Thereafter, the resulting filtrate is concentrated into a concentrated solution with relative density of about 1.2 g/cm³ (45-50° C.) and the weight of the concentrated solution is 40 g. The weighed *Triticum Aestivum* is pulverized into particles of about 30 mesh size, and the concentrated solution is sprayed into the pulverized particles of *Triticum Aestivum* by utilizing flow layer drying equipment. The pulverized particles of *Triticum Aestivum* loaded with the concentrated solution are fully dried into 20 g of final product, which is packed in tea bags of 2 grams/bag and 10 bags/box.

In this example, *Semen Lablab Album* is added into the basic formula of herbal tea of the present invention. Therefore, the herbal tea prepared in this example not only has the essential functions described in the invention, but also can strengthen the effect of invigorating spleen for eliminating dampness, and the effect of regulating stomach and clearing summer heat.

The invention claimed is:

1. A method of preparing an herbal tea for use as a milk supplement comprising the following medicinal materials: Raw *Semen Coicis*, *Herba Lophatheri*, *Setaria Italica*, Prepared *Semen Coicis*, *Fructus Hordei* Germinatus, *Fructus Setariae* Germinatus, *Medulla Junci* and *Triticum Aestivum*, wherein the *Triticum Aestivum* is used as a forming agent in the herbal tea, wherein the method comprises:
(a) weighing the medicinal materials, wherein the weight percentages of the medicinal materials are as follows: 20-35% of Raw *Semen Coicis*, 5-15% of *Herba Lophatheri*, 5-15% of *Setaria Italica*, 5-15% of Prepared *Semen Coicis*, 4-12% of *Fructus Hordei* Germinatus, 4-12% of *Fructus Setariae* Germinatus, 0.2-2% of *Medulla Junci* and 15-25% of *Triticum Aestivum*, based on the total weight of the medicinal materials;
(b) mixing the medicinal materials except for *Triticum Aestivum* together, decocting the resulting mixture with water 1-3 time(s), wherein each decocting steps lasts for 0.5-2 hours;
(c) combining the decoctions obtained from step (b), filtering, and concentrating the resulting filtrate into a concentrated solution with relative density of 1.0-1.3 g/cm³;
(d) pulverizing the weighed *Triticum Aestivum* into particles of 15-40 mesh size, and then dispersing the concentrated solution obtained from the step (c) to the pulverized particles of *Triticum Aestivum*; and
(e) fully drying the pulverized particles of *Triticum Aestivum* comprising the concentrated solution obtained from the step (d), and then packing the particles in a desired product form.

2. The method according to claim 1, wherein the method comprises:
(b) decocting the resulting mixture with water 2 times, wherein each decocting step lasts for 1 hour; and
(c) combining the decoctions obtained from step (b), filtering, and concentrating the filtrate into a concentrated solution with relative density of 1.1-1.2 g/cm³.

3. The method according to claim 2, wherein the step (d) comprises pulverizing the weighed *Triticum Aestivum* into particles of 25-35 mesh size, and then spraying the concentrated solution obtained from step (c) to the pulverized particles of *Triticum Aestivum* by utilizing flow layer drying equipment.

4. The method according to claim 3, wherein the *Triticum Aestivum* is pulverized into about 30 mesh size in the step (d).

5. The method according to claim 4, wherein the pulverized *Triticum Aestivum* is packed in tea bags in the step (e).

6. The method according to claim 1, wherein the weight percentages of the medicinal materials are as follows: 22-32% of Raw *Semen Coicis*, 8-15% of *Herba Lophatheri*, 8-15% of *Setaria Italica*, 6-12% of Prepared *Semen Coicis*, 5-10% of *Fructus Hordei* Germinatus, 5-10% of *Fructus Setariae* Germinatus, 0.2-1% of *Medulla Junci* and 18-22% of *Triticum Aestivum*, based on the total weight of the medicinal materials.

7. The method according to claim 1, wherein the weight percentages of the medicinal materials are as follows: 29.10% of Raw *Semen Coicis*, 12.60% of *Herba Lophatheri*, 12.60% of *Setaria Italica*, 10.10% of Prepared *Semen Coicis*, 7.60% of *Fructus Hordei* Germinatus, 7.60% of *Fructus Setariae* Germinatus, 0.40% of *Medulla Junci* and 20.00% of *Triticum Aestivum*.

8. The method according to claim 1, wherein the herbal tea for use as a milk supplement further comprises *Pseudostellariae Radix*.

9. The method according to claim 1, wherein the herbal tea for use as a milk supplement further comprises *Radix Ophiopogonis*.

10. The method according to claim 1, wherein the herbal tea for use as a milk supplement further comprises *Semen Lablab Album*.

\* \* \* \* \*